United States Patent [19]

Failli et al.

[11] Patent Number: 5,120,842

[45] Date of Patent: Jun. 9, 1992

[54] SILYL ETHERS OF RAPAMYCIN

[75] Inventors: Amedeo A. Failli, Princeton Junction, N.J.; Robert J. Steffan, Langhorne, Pa.

[73] Assignee: American Home Products Corporation, New York, N.Y.

[21] Appl. No.: 678,380

[22] Filed: Apr. 1, 1991

[51] Int. Cl.⁵ .................. A61K 31/395; C07D 491/06
[52] U.S. Cl. .................. 540/452; 540/456; 546/90; 514/63; 514/183
[58] Field of Search .................. 540/452, 456; 514/63, 514/183, 321, 291; 546/90

[56] References Cited

U.S. PATENT DOCUMENTS

| | | | |
|---|---|---|---|
| 3,929,992 | 12/1975 | Sehgal et al. | 424/122 |
| 3,993,749 | 11/1976 | Sehgal et al. | 424/122 |
| 4,316,885 | 2/1982 | Rakhit | 424/122 |
| 4,401,653 | 8/1983 | Eng | 424/114 |
| 4,650,803 | 3/1987 | Stella et al. | 546/90 |
| 4,885,171 | 12/1989 | Surendra et al. | 424/122 |

OTHER PUBLICATIONS

J. Antibiot. 28, 721-726 727-732 (1975).
J. Antibiot. 31, 539-545 (1978).
Can. J. Physiol. Pharmacol. 55, 48 (1977).
FASEB 3, 3411, 5256. (1989).
Lancet 1183 (1978).
Med. Sci. Res. 17: 877 (1989).
J. Am. Chem. Soc. 103: 3215 (1981).
J. Am. Chem. Soc. 94: 6190 (1972).

Primary Examiner—Robert T. Bond
Attorney, Agent, or Firm—Arnold S. Milowsky

[57] ABSTRACT

A compound of the structure

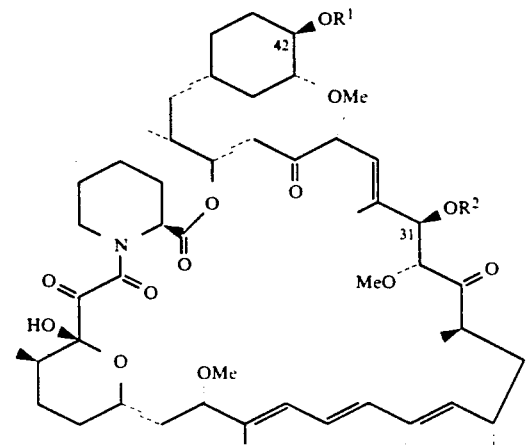

wherein
 $R^1$ is $-SiR^3R^4R^5$;
 $R^2$ is hydrogen or $-SiR^3R^4R^5$; and
 $R^3$, $R^4$, and $R^5$ are each, independently, alkyl, alkenyl, aralkyl, triphenylmethyl, or phenyl which by virtue of its immunosuppressive activity is useful in treating transplantation rejection, host vs. graft disease, autoimmune diseases and diseases of inflammation; by virtue of its antitumor activity is useful in treating solid tumors; and by virtue of its antifungal activity is useful in treating fungal infections. This invention also provides a method of using rapamycin 42-[O-[(1,1-dimethylethyl)-dimethylsilyl] ether for the preparation of 31-substituted rapamycin derivatives.

9 Claims, No Drawings

SILYL ETHERS OF RAPAMYCIN

BACKGROUND OF THE INVENTION

This invention relates to silyl ethers of rapamycin and a method for using them in the treatment of transplantation rejection, host vs. graft disease, autoimmune diseases, diseases of inflammation, solid tumors, and fungal infections.

Rapamycin is a macrocyclic triene antibiotic produced by *Streptomyces hygroscopicus*, which was found to have antifungal activity, particularly against *Candida albicans*, both in vitro and in vivo [C. Vezina et al., J. Antibiot. 28, 721 (1975); S. N. Sehgal et al., J. Antibiot. 28, 727 (1975); H. A. Baker et al., J. Antibiot. 31, 539 (1978); U.S. Pat. No. 3,929,992; and U.S. Pat. No. 3,993,749].

Rapamycin alone (U.S. Pat. No. 4,885,171) or in combination with picibanil (U.S. Pat. No. 4,401,653) has been shown to have antitumor activity. R. Martel et al. [Can. J. Physiol. Pharmacol. 55, 48 (1977)] disclosed that rapamycin is effective in the experimental allergic encephalomyelitis model, a model for multiple sclerosis; in the adjuvant arthritis model, a model for rheumatoid arthritis; and effectively inhibited the formation of IgE-like antibodies.

The immunosuppressive effects of rapamycin have been disclosed in FASEB 3, 3411 (1989). Cyclosporin A and FK-506, other macrocyclic molecules, also have been shown to be effective as immunosuppressive agents, therefore useful in preventing transplant rejection [FASEB 3, 3411 (1989); FASEB 3, 5256 (1989); and R. Y. Calne et al., Lancet 1183 (1978)].

Mono- and diacylated derivatives of rapamycin (esterified at the 28 and 43 positions) have been shown to be useful as antifungal agents (U.S. Pat. No. 4,316,885) and used to make water soluble prodrugs of rapamycin (U.S. Pat. No. 4,650,803). Recently, the numbering convention for rapamycin has been changed; therefore according to Chemical Abstracts nomenclature, the esters described above would be at the 31- and 42-positions.

DESCRIPTION OF THE INVENTION

This invention provides derivatives of rapamycin which are useful as immunosuppressive, anti-inflammatory, antifungal, and antitumor agents having the structure

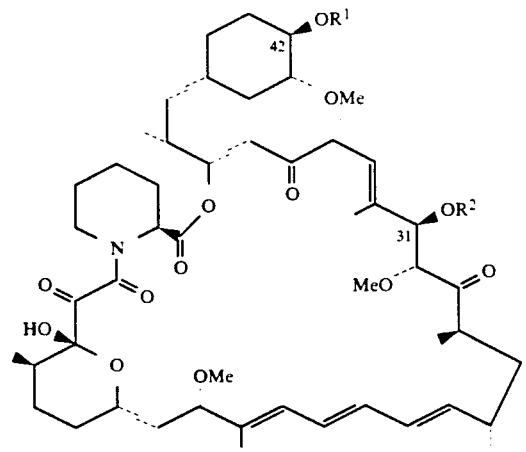

wherein
$R^1$ is $-SiR^3R^4R^5$;
$R^2$ is hydrogen or $-SiR^3R^4R^5$; and
$R^3$, $R^4$, and $R^5$ are each, independently, alkyl of 1-8 carbon atoms, alkenyl of 1-8 carbon atoms, aralkyl of 7-10 carbon atoms, triphenylmethyl, or phenyl.

Of these compounds, preferred members are those in which $R^2$ is hydrogen; those in which $R^2$ is hydrogen and $R^3$, $R^4$, and $R^5$ are alkyl of 1-8 carbon atoms; and those in which $R^3$, $R^4$, and $R^5$ are alkyl of 1-8 carbon atoms.

The compounds of this invention that are silylated at the 42-position can be prepared by reacting an approximately equimolar quantity of rapamycin and an appropriately substituted silyl halide in the presence of a base such as imidazole. [See, E. J. Corey, J. Am. Chem. Soc. 94, 6190 (1972)].

It was surprising that the 42-position could be selectively silylated in the presence of the other hydroxyl groups at the 14- and 31-positions of rapamycin as functional group reactivity cannot be readily predicted in a poly-functionalized macrocyclic ring. [R. B. Woodward et al., J. Am. Chem. Soc. 103, 3215 (1981)].

Compounds silylated at both the 31- and 42-positions can be prepared by reacting rapamycin, in the presence of a suitable base such as imidazole, with an excess of silylating reagent.

The silylating reagents used to prepare the compounds of the invention are commercially available or can be prepared by methods that are disclosed in the literature.

Immunosuppressive activity was evaluated in an in vitro standard pharmacological test procedure to measure lymphocyte proliferation (LAF).

The comitogen-induced thymocyte proliferation procedure (LAF) was used as an in vitro measure of the immunosuppressive effects of representative compounds. Briefly, cells from the thymus of normal BALB/c mice are cultured for 72 hours with PHA and IL-1 and pulsed with tritiated thymidine during the last six hours. Cells are cultured with and without various concentrations of rapamycin, cyclosporin A, or test compound. Cells are harvested and incorporated radioactivity is determined. Inhibition of lymphoproliferation is assessed as percent change in counts per minute from non-drug treated controls. The results are expressed as an $IC_{50}$.

The following table summarizes the results of a representative compound of this invention in the LAF standard test procedure.

| Compound | $IC_{50}$ (nM) |
| --- | --- |
| Example 1 | 45.8 |
| Rapamycin | 3.2 |

The results of this standard pharmacological test procedure for a representative compound of this invention demonstrates that the compounds of this invention are useful as immunosuppressive agents.

Antifungal activity of a representative compound of this invention was measured against 5 strains of *Candida albicans* using a plate test procedure for measurement of inhibition. The following represents the typical procedure used. Compound to be tested was placed on sterile dried ¼" plate disks, and allowed to dry. Agar plates were seeded with fungi and allowed to solidify. The impregnated disks were placed on the seeded Agar surface and incubated for the time required for the particular culture. The following table shows the results obtained in this standard pharmacological test procedure for antifungal activity and are expressed in MIC (μg/ml) to inhibit growth.

| | Strain of *Candida albicans* | | | | |
| --- | --- | --- | --- | --- | --- |
| Compound | ATCC 10231 | ATCC 38246 | ATCC 38247 | ATCC 38248 | 3669 |
| Example 1 | 0.2 | >0.4 | 0.2 | >0.4 | >0.4 |
| Rapamycin | 0.003 | 0.025 | 0.003 | 0.006 | 0.025 |

The results of this standard pharmacological test procedure for a representative compound of this invention demonstrates that the compounds of this invention are useful as antifungal agents.

Because the compounds of this invention are structurally similar to rapamycin and have a similar activity profile to rapamycin, the compounds of this invention also are considered to have antitumor activity.

Based on the results of these standard pharmacological test procedures, the compounds of this invention are useful in the treatment of transplantation rejection such as, heart, kidney, liver, bone marrow, and skin transplants; autoimmune diseases such as, lupus, rheumatoid arthritis, diabetes mellitus, myasthenia gravis, and multiple sclerosis; and diseases of inflammation such as, psoriasis, dermatitis, eczema, seborrhea, inflammatory bowel disease, and eye uveitis; solid tumors; and fungal infections.

In addition, this invention provides a method of using the compound of Example 1 in the selective preparation of 31-substituted derivatives of rapamycin. This process is described below.

When rapamycin is reacted with one equivalent of tert-butyl dimethylsilyl chloride the 42-position is selectively silylated, thus leaving the 31-position available for subsequent reaction with a suitable electrophilic reagent. For example, when acetic anhydride is used as the electrophile, the corresponding 42-silylated, 31-acetylrapamycin is formed. The 42-position can then be deprotected under mild conditions, such as with acetic acid to provide derivatives of rapamycin substituted at the 31-position.

This process therefore provides a general method of selectively preparing 31-substituted derivatives of rapamycin, thereby eliminating the need for chromatographic separation of the 31-derivatives from a mixture of 31-, 42-, and 31,42-substituted rapamycins when rapamycin is simply reacted with an electrophile.

A representative compound, rapamycin-31-acetate was prepared by the above process and is useful as immunosuppressive agent by virtue of its activity in the LAF standard pharmacological test procedure described above. The $IC_{50}$ for this compound in the LAF procedure was 56.5 nM, whereas rapamycin had an $IC_{50}$ of 7.8 nM when evaluated contemporaneously with rapamycin-31-acetate. Because this compound structurally similar to rapamycin and has a similar activity profile to rapamycin in the LAF procedure, it is considered to have antitumor and antifungal activities. The intermediate, rapamycin 42-[O-[(1,1-Dimethylethyl)dimethylsilyl]]ether-31-acetate, is also considered to have the same activity profile as stated above.

The compounds of this invention may be administered neat or with a pharmaceutical carrier to a mammal in need thereof. The pharmaceutical carrier may be solid or liquid.

A solid carrier can include one or more substances which may also act as flavoring agents, lubricants, solubilizers, suspending agents, fillers, glidants, compression aids, binders or tablet-disintegrating agents; it can also be an encapsulating material. In powders, the carrier is a finely divided solid which is in admixture with the finely divided active ingredient. In tablets, the active ingredient is mixed with a carrier having the necessary compression properties in suitable proportions and compacted in the shape and size desired. The powders and tablets preferably contain up to 99% of the active ingredient. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

Liquid carriers are used in preparing solutions, suspensions, emulsions, syrups, elixirs and pressurized compositions. The active ingredient can be dissolved or suspended in a pharmaceutically acceptable liquid carrier such as water, an organic solvent, a mixture of both or pharmaceutically acceptable oils or fats. The liquid carrier can contain other suitable pharmaceutical additives such as solubilizers, emulsifiers, buffers, preservatives, sweeteners, flavoring agents, suspending agents, thickening agents, colors, viscosity regulators, stabilizers or osmo-regulators. Suitable examples of liquid carriers for oral and parenteral administration include water (partially containing additives as above, e.g. cellulose derivatives, preferably sodium carboxymethyl cellulose solution), alcohols (including monohydric alcohols and polyhydric alcohols, e.g. glycols) and their derivatives, and oils (e.g. fractionated coconut oil and arachis oil). For parenteral administration, the carrier can also be an oily ester such as ethyl oleate and isopropyl myristate. Sterile liquid carriers are useful in sterile liquid form compositions for parenteral administration. The liquid carrier for pressurized compositions can be halogenated hydrocarbon or other pharmaceutically acceptable propellent.

Liquid pharmaceutical compositions which are sterile solutions or suspensions can be utilized by, for example, intramuscular, intraperitoneal or subcutaneous injection. Sterile solutions can also be administered intravenously. The compound can also be administered orally either in liquid or solid composition form.

Preferably, the pharmaceutical composition is in unit dosage form, e.g. as tablets or capsules. In such form, the composition is sub-divided in unit dose containing appropriate quantities of the active ingredient; the unit dosage forms can be packaged compositions, for example, packeted powders, vials, ampoules, prefilled syringes or sachets containing liquids. The unit dosage form can be, for example, a capsule or tablet itself, or it can be the appropriate number of any such compositions in package form. The dosage to be used in the treatment must be subjectively determined by the attending physician.

In addition, the compounds of this invention may be employed as a solution, cream, or lotion by formulation with pharmaceutically acceptable vehicles containing 0.1-0.5 percent, preferably 2%, of active compound which may be administered to a fungally affected area.

The following examples illustrate the preparation of representative compounds of this invention.

EXAMPLE 1

Rapamycin 42-O-[(1,1-Dimethylethyl)dimethylsilyl]ether

Tert-butyldimethylsilyl chloride (0.8 g, 5.4 mmole) was added in one portion to a solution of rapamycin (5 g, 5.4 mmole) and imidazole (1.1 g, 16.2 mmole) in 20 mL of dry DMF kept under nitrogen. After stirring at room temperature for 72 hours, the reaction mixture was diluted with water and stirred another 15 min. The precipitated solid was collected, washed with water and dried in vacuo to give 5.5 g of the title compound.

$^1$H NMR (CDCl$_3$, 400 MHz): δ0.0 (m, 6H, SiCH$_3$), 0.869 (s, 9H, tert-Bu), 1.63 (s, 3H, CH$_3$C=C), 1.72 (m, 3H, CH$_3$C=C), 3.12 (s, 3H, CH$_3$O), 3.32 (s, 3H, CH$_3$O), 3.394 (s, 3H, CH$_3$O).

MS (neg. ion FAB, m/z): 1028 (M)$^-$, 590, 435

Anal. Calc'd for C$_{57}$H$_{93}$NO$_{13}$Si: C, 66.57; H, 9.11; N, 1.36. Found: C, 66.06; H, 9.23; N, 1.25.

The following representative compounds can be prepared from rapamycin and the appropriate silyl halide by employing the method used to prepare the title compound in Example 1.

Rapamycin 42-O-trimethylsilyl ether
Rapamycin 42-O-triphenylsilyl ether
Rapamycin 42-O-triisopropylsilyl ether
Rapamycin 42-O-[(1,1-dimethylethyl)diphenylsilyl ether
Rapamycin 42-O-tri-(phenylmethyl)silyl ether
Rapamycin 42-O-(triphenylmethyl)dimethylsilyl ether
Rapamycin 42-O-phenyldimethylsilyl ether
Rapamycin 42-O-allyldimethylsilyl ether
Rapamycin 42-O-octyldimethylsilyl ether

EXAMPLE 2

Rapamycin 42-O-[(1,1-Dimethylethyl)dimethylsilyl]ether-31-acetate

Under anhydrous conditions, acetic anhydride (0.091 mL, 0.97 mmole) was added in one portion to a stirred solution of rapamycin 42-[O-[(1,1-Dimethylethyl)dimethylsilyl]ether (1.0 g, 0.97 mmole) containing 4-dimethylaminopyridine (DMAP, 0.24 g, 2 mmole) in 20 mL of dry dichloromethane. The solution was stirred at room temperature overnight and then poured onto a 15 g plug of silica gel. The gel was washed with additional dichloromethane containing a trace of methanol. Evaporation of the filtrate under reduced pressure provides 1.1 g of crude product as a yellow foam. Purification of this material by HPLC [silica gel 8μ, Dynamax 60A 41 mm×250 mm column, hexane-ethyl acetate 3:7 to 1:1, flow rate 30 mL/min, UV detector at 280 nm] gives pure product as a white solid (0.25 g, 24%).

$^1$H NMR (CDCl$_3$, 400 MHz): δ0.04 (m, 6H, SiCH$_3$), 0.861 (s, 9H, tert-Bu), 1.64 (s, 3H, CH$_3$C=C), 1.738 and 1.741 (2s, 3H, CH$_3$C=C), 2.01 (s, 3H, COCH$_3$), 3.125 (s, 3H, CH$_3$O), 3.31 (s, 3H, CH$_3$O), 3.395 (s, 3H, CH$_3$O).

$^{13}$C NMR (CDCl$_3$, 400 MHz): 212.4, 211, 207.9, 206.76, 196.13, 192.92, 169.38, 169.27, 169.17, 166.55, 165.83, 98.47

MS (neg. ion FAB, m/z): 1070 (M)$^-$

Anal. Calc'd for C$_{59}$H$_{95}$NO$_{14}$Si: C, 66.19; H, 8.96; N, 1.31. Found: C, 65.83; H, 8.91; N, 1.35.

EXAMPLE 3

Rapamycin 31-acetate

A solution of rapamycin 42-[O-[(1,1-Dimethylethyl)-dimethylsilyl]ether-31-acetate (0.125 g, 0.12 mmole) in 1.0 mL of acetic acid/water/THF (3:1:1, v/v/v) was stirred at room temperature for 18 hours. The reaction mixture was diluted with water and stirred. The precipitated solid was collected, washed with water and dried in vacuo. The crude material was purified by flash chromatography (on silica Merck-60, eluant dichloromethane-methanol 25:1) to provide the pure product as a white solid (0.045 g, 39%).

$^1$H NMR (CDCl$_3$, 400 MHz): δ1.64 (s, 3H, CH$_3$C=C), 1.746 and 1.748 (2s, 3H, CH$_3$C=C), 2.018 (s, 3H, COCH$_3$), 3.125 (s, 3H, CH$_3$O), 3.32 (s, 3H, CH$_3$O), 3.39 (s, 3H, CH$_3$O).

MS (neg. ion FAB, m/z): 956 (M)$^-$

EXAMPLE 4

Rapamycin 31,42-bis-O-[(1,1-Dimethylethyl)dimethylsilyl]ether

Excess tert-butyldimethylsilyl chloride (0.66 g, 4.4 mmole) was added in one portion to a solution of rapamycin (1.0 g, 1.1 mmole) and imidazole (1.0 g, 15 mmole) in 3 mL of dry DMF kept under nitrogen. After stirring at room temperature for 48 hours, the reaction mixture was diluted with water (100 mL) and stirred for an additional 15 min. The precipitated solid was collected, washed with water and dried in vacuo. This material (1.5 g, off-white solid) was further purified by flash chromatography (on silica Merck-60, eluant hexane-ethylacetate 1:1) to provide the title compound as a white solid (0.13 g, 10%).

$^1$H NMR (CDCl$_3$, 400 MHz): δ0.14 (m, 6H, SiCH$_3$), 0.926 (s, 9H, tert-Bu), 1.722 (s, 3H, CH$_3$C=C), 1.812 and 1.814 (2s, 3H, CH$_3$C=C), 3.205 (s, 3H, CH$_3$O), 3.343 (s, 3H, CH$_3$O), 3.479 (s, 3H, CH$_3$O).

MS (neg. ion FAB, m/z): 1141 (M)$^-$

Anal. Calc'd for C$_{63}$H$_{107}$NO$_{13}$Si$_2$+2H$_2$O: C, 64.20; H, 9.49; N, 1.19. Found: C, 64.25; H, 9.56; N, 1.07.

The following representative compounds can be prepared from rapamycin and the appropriate silyl halide by employing the method used to prepare the title compound in Example 4.

Rapamycin 31,42-bis-O-trimethylsilyl ether
Rapamycin 31,42-bis-O-triphenylsilyl ether
Rapamycin 31,42-bis-O-triisopropylsilyl ether
Rapamycin 31,42-bis-O-[(1,1-dimethylethyl)diphenylsilyl ether
Rapamycin 31,42-bis-O-tri-(phenylmethyl)silyl ether
Rapamycin 31,42-bis-O-(triphenylmethyl)dimethylsilyl ether Rapamycin 31,42-bis-O-phenyldimethylsilyl ether
Rapamycin 31,42-bis-O-allyldimethylsilyl ether
Rapamycin 31,42-bis-O-octyldimethylsilyl ether

What is claimed is:

1. A compound of the formula

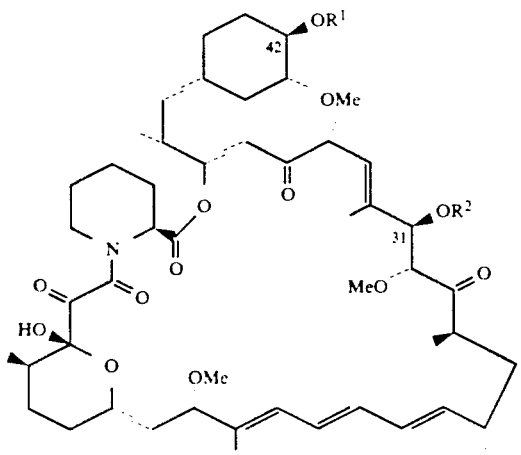

wherein

R$^1$ is —SiR$^3$R$^4$R$^5$;

R$^2$ is hydrogen or —SiR$^3$R$^4$R$^5$; and

R$^3$, R$^4$, and R$^5$ are each, independently, alkyl of 1–8 carbon atoms, alkenyl of 1–8 carbon atoms, phenylalkyl of 7–10 carbon atoms, triphenylmethyl, or phenyl.

2. A compound of claim 1 in which R$^2$ is hydrogen.

3. A compound of claim 1 in which R$^2$ is hydrogen and R$^3$, R$^4$, and R$^5$ are alkyl of 1–8 carbon atoms.

4. A compound of claim 1 in which R$^3$, R$^4$, and R$^5$ are alkyl of 1–8 carbon atoms.

5. A compound of claim 1 which is rapamycin 42-O-[(1,1-dimethylethyl)dimethylsilyl]ether.

6. A compound of claim 1 which is rapamycin 31,42-bis-O-[(1,1-dimethylethyl)dimethylsilyl]ether.

7. A method of using rapamycin 42-O-[(1,1-dimethylethyl)-dimethylsilyl]ether for the preparation of a 31-acylated rapamycin which comprises reacting rapamycin 42-O-[(1,1-dimethylethyl)-dimethylsilyl]ether with an acylating agent to give an intermediate in which the 31-alcohol of rapamycin has reacted with the acylating agent and the 42-position is protected as the 42-[O-[(1,1-dimethylethyl)dimethylsilyl]ether; and subsequent hydrolysis of the 42-silyl ether to provide the 31-acylated rapamycin.

8. A compound which is rapamycin 42-[O-[(1,1-Dimethylethyl)dimethylsilyl]ether-31-acetate.

9. A compound which is rapamycin-31-acetate.

* * * * *

REEXAMINATION CERTIFICATE (2056th)
United States Patent
Failli et al.

[11] B1 5,120,842
[45] Certificate Issued Jul. 6, 1993

[54] SILYL ETHERS OF RAPAMYCIN

[75] Inventors: Amedeo A. Failli, Princeton Junction, N.J.; Robert J. Steffan, Langhorne, Pa.

[73] Assignee: American Home Products Corporation, New York, N.Y.

Reexamination Request:
No. 90/002,871, Oct. 20, 1992

Reexamination Certificate for:
Patent No.: 5,120,842
Issued: Jun. 9, 1992
Appl. No.: 678,380
Filed: Apr. 1, 1991

[51] Int. Cl.$^5$ .................. A61K 31/395; C07D 491/16
[52] U.S. Cl. .................... 540/452; 540/456; 546/90; 514/63; 514/291; 514/411; 514/183
[58] Field of Search ........................ 540/452, 456

[56] References Cited
PUBLICATIONS

Goulet, M. et al., Tetrahedron Let., vol. 31: p. 4845 (1990) (Attachment A).

*Primary Examiner*—Robert T. Bond

[57] ABSTRACT

A compound of the structure

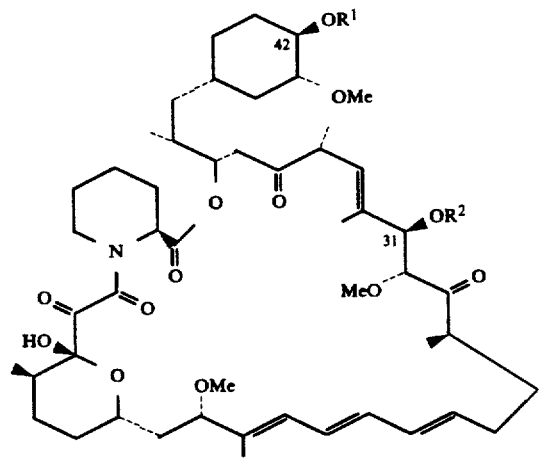

wherein
$R^1$ is $-SiR^3R^4R^5$;
$R^2$ is hydrogen or $-SiR^3R^4R^5$; and
$R^3$, $R^4$, and $R^5$ are each, independently, alkyl, alkenyl, aralkyl, triphenylmethyl, or phenyl which by virtue of its immunosuppressive activity is useful in treating transplantation rejection, host vs. graft disease, autoimmune diseases and diseases of inflammation; by virtue of its antitumor activity is useful in treating solid tumors; and by virtue of its antifungal activity is useful in treating fungal infections. This invention also provides a method of using rapamycin 42-[O-[(1,1-dimethylethyl)-dimethylsilyl] ether for the preparation of 31-substituted rapamycin derivatives.

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

The patentability of claims 4, 5, 7, 8 and 9 is confirmed.

Claims 2, 3 and 6 having been finally determined to be unpatentable, are cancelled.

Claim 1 is determined to be patentable as amended.

1. A compound of the formula

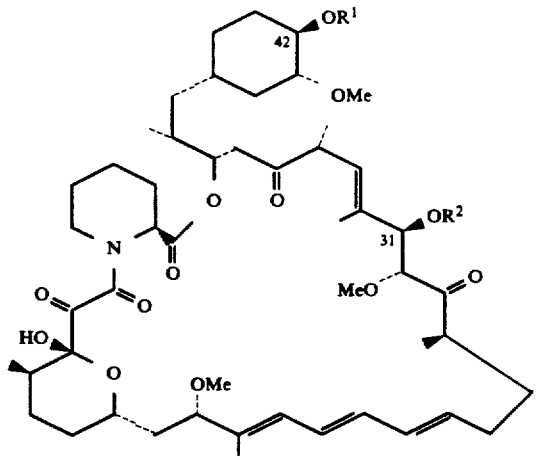

wherein $R^1$ is $-SiR^3R^4R^5$;
$R^2$ is hydrogen [or $-SiR^3R^4R^5$];
and $R^3$, $R^4$, and $R^5$ are each, independently, alkyl of 1-8 carbon atoms, alkenyl of 1-8 carbon atoms, phenylalkyl of 7-10 carbon atoms, triphenylmethyl, or phenyl.

* * * * *